US006296666B1

(12) United States Patent
Gardner

(10) Patent No.: US 6,296,666 B1
(45) Date of Patent: Oct. 2, 2001

(54) MOBILE BEARING KNEE WITH CENTER POST

(75) Inventor: Kenneth Jay Gardner, Georgetown, TX (US)

(73) Assignee: Encore Medical Corporation, Austin, TX (US)

( * ) Notice: Subject to any disclaimer, the term of this patent is extended or adjusted under 35 U.S.C. 154(b) by 0 days.

(21) Appl. No.: 09/524,386

(22) Filed: Mar. 13, 2000

(51) Int. Cl.$^7$ ........................................... A61F 2/38
(52) U.S. Cl. ............................. 623/20.29; 623/20.33
(58) Field of Search .......................... 623/20.14, 20.15, 623/20.21, 20.28, 20.29, 20.33

(56) References Cited

U.S. PATENT DOCUMENTS

| | | |
|---|---|---|
| 4,224,697 | 9/1980 | Murray et al. . |
| 4,950,297 | 8/1990 | Elloy et al. . |
| 5,314,480 | 5/1994 | Elloy et al. . |
| 5,683,468 | 11/1997 | Pappas . |
| 5,755,801 | 5/1998 | Walker et al. . |
| 5,766,257 | 6/1998 | Goodman et al. . |
| 5,871,543 | 2/1999 | Hofmann . |
| 5,871,545 | 2/1999 | Goodfellow et al. . |
| 5,906,643 | 5/1999 | Walker . |
| 5,928,286 | 7/1999 | Ashby et al. . |
| 5,937,530 | 8/1999 | Masson . |
| 5,957,979 | 9/1999 | Beckman et al. . |
| 6,010,534 | 1/2000 | O'Neil et al. . |
| 6,123,728 | * 9/2000 | Brosnahan et al. ............. 623/20.24 |

* cited by examiner

Primary Examiner—Bruce Snow
Assistant Examiner—Brian Pellegrino
(74) Attorney, Agent, or Firm—Larson & Taylor, PLC

(57) ABSTRACT

A mobile bearing knee prosthesis in which the tibial component includes an upstanding post and a cap provided at an upper end thereof. The cap includes a lip extending laterally outward from the post to give the cap a generally oval shape with a major axis in the A/P direction and a minor axis in the M/L direction. The meniscal insert includes an undercut cavity elongated in the A/P direction in which the post is received. The undercut cavity has a length allowing substantial movement of the post therealong in the A/P direction, and a width allowing only a minor movement of the post in the M/L direction. The insert also includes an upper cutout extending around an upper portion of the cavity which receives therein an adjacent portion of the lip. With this construction, the insert and the baseplate are free to slide relative to one another along a plane of contact therebetween, except when constrained by (i) a contact of the post with the undercut cavity as movement occurs in the A/P and M/L directions, whereby substantial relative movement of the insert and baseplate in the A/P direction is allowed and only a minor relative movement in the M/L direction is allowed, and (ii) an engagement of the lip located between the minor axis and the major axis with the upper cutout as rotation occurs about an axis perpendicular to the plane of contact, whereby only some predetermined rotational relative movement is allowed.

10 Claims, 5 Drawing Sheets

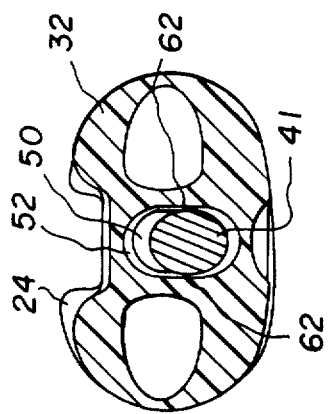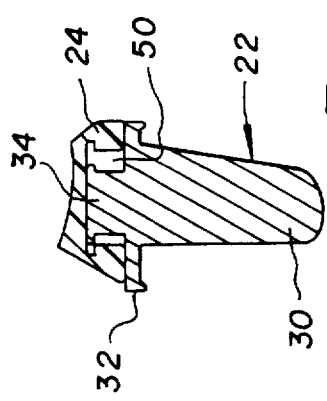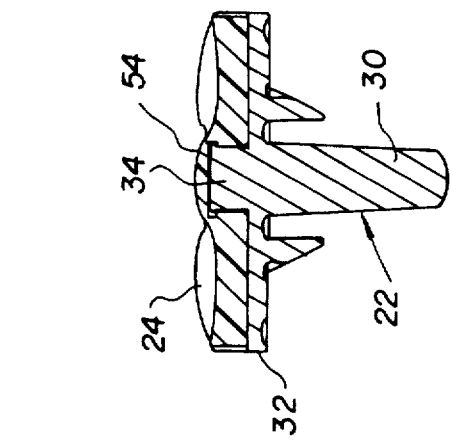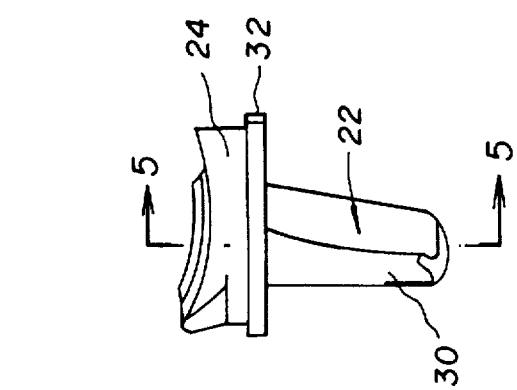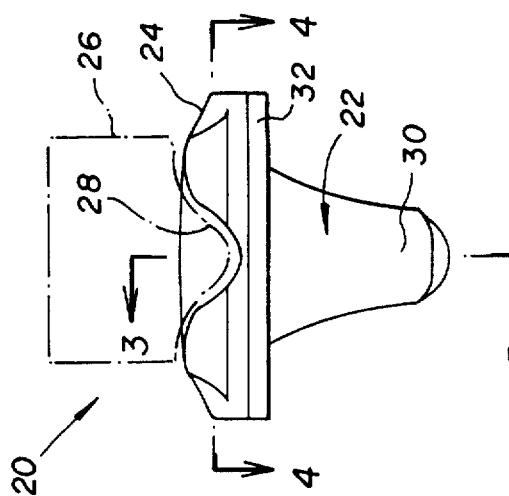

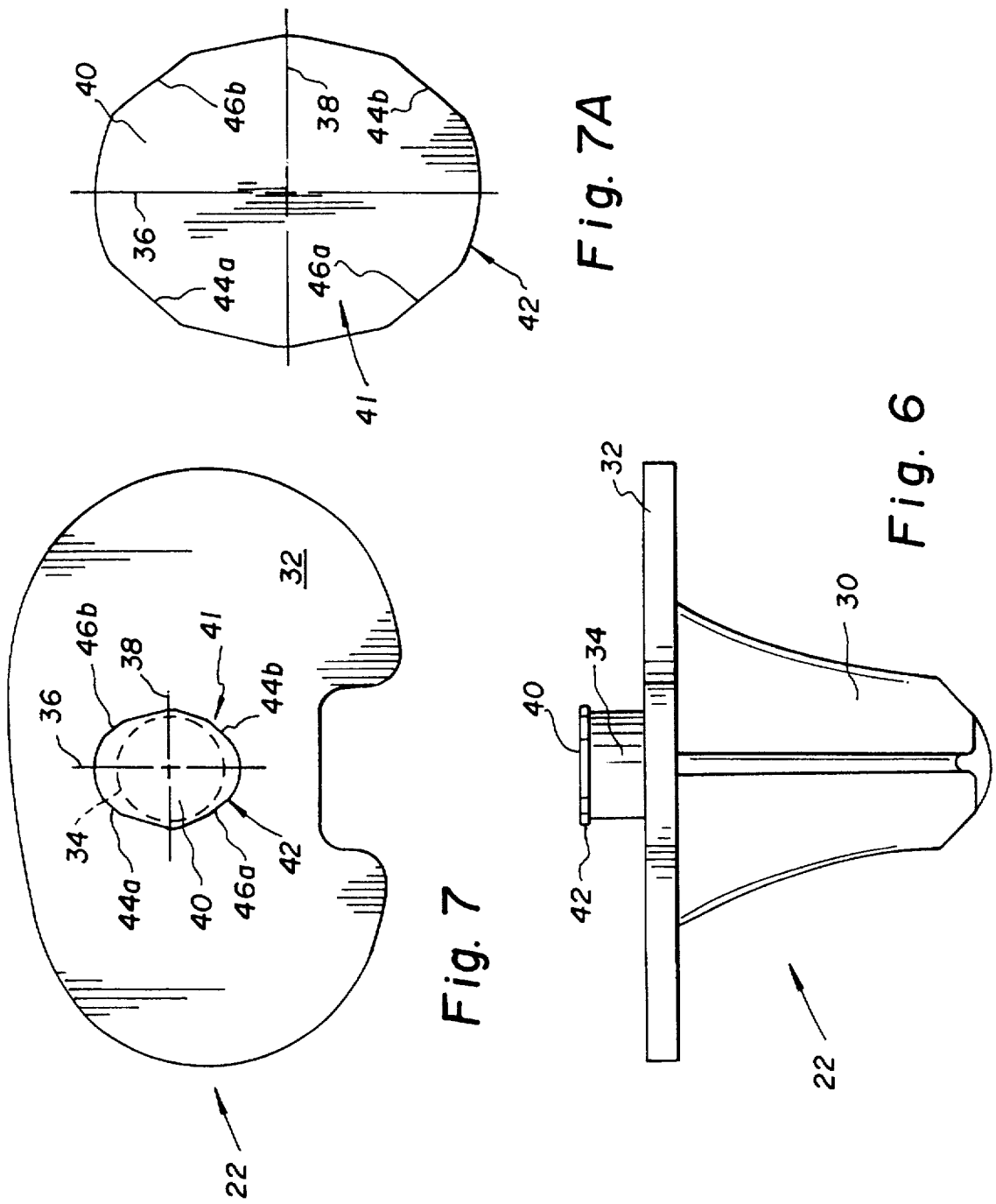

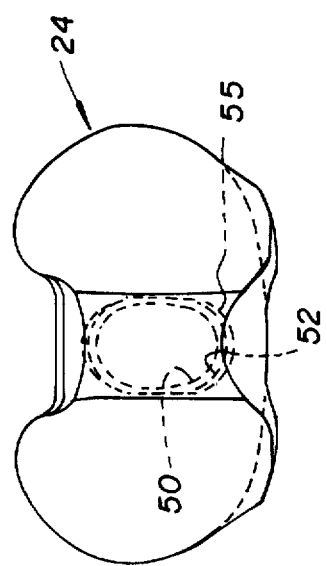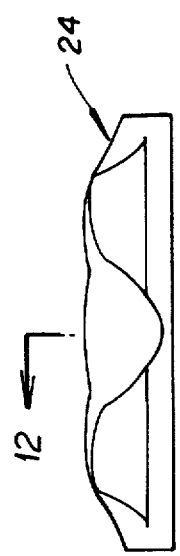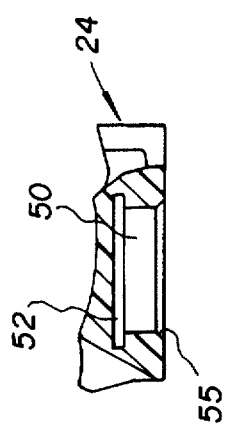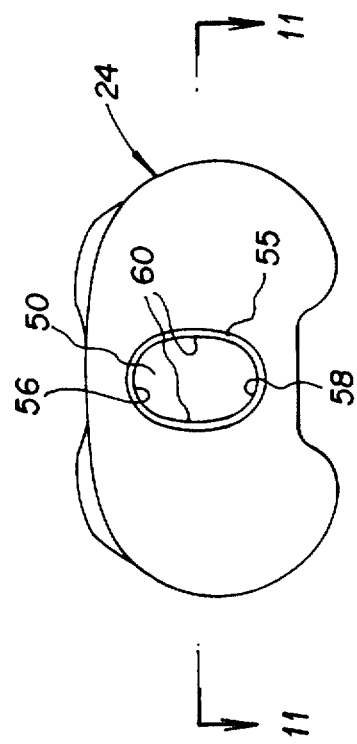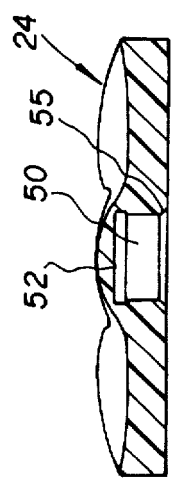

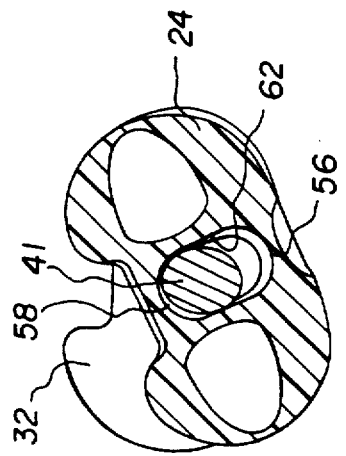
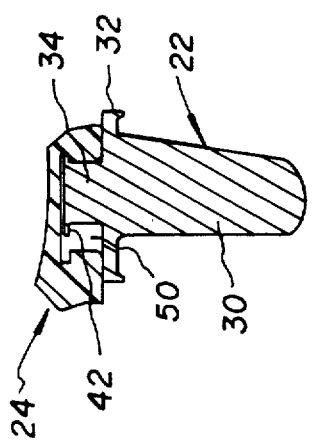
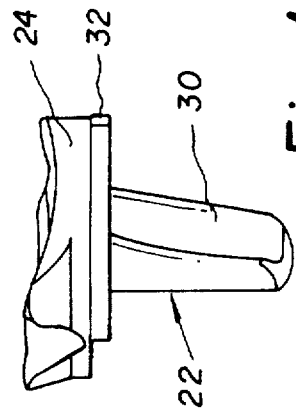
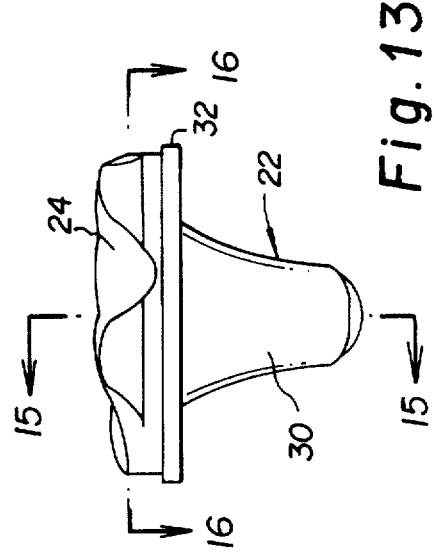

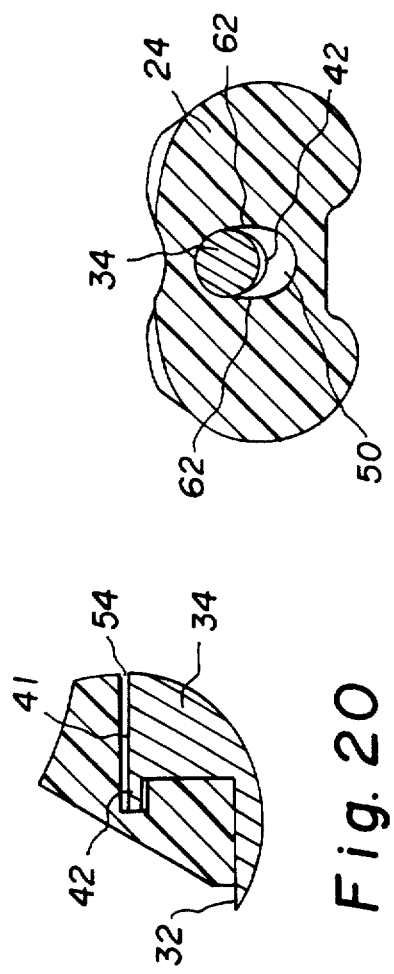
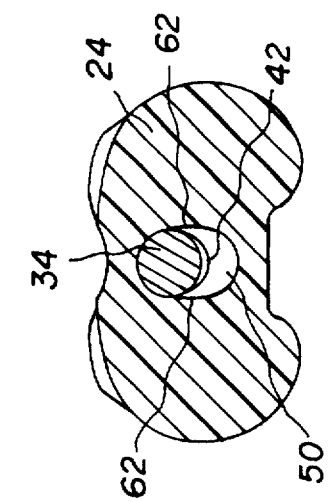
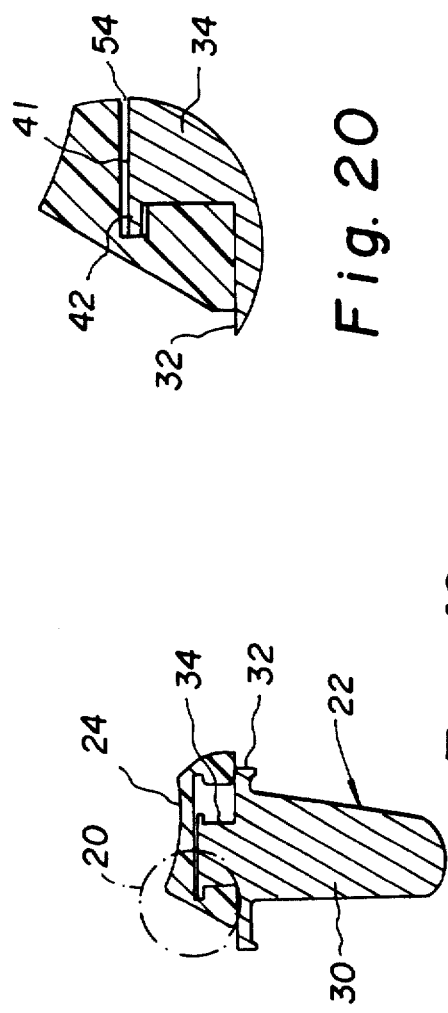
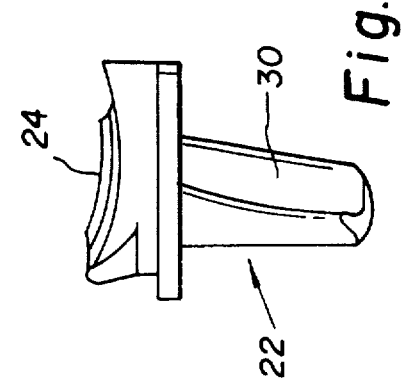
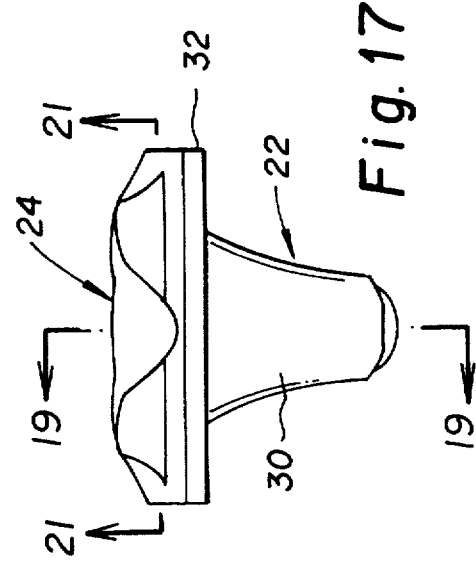

MOBILE BEARING KNEE WITH CENTER POST

FIELD OF THE INVENTION

The present invention relates generally to knee prostheses, and more particularly to a mobile knee prosthesis allowing substantial A/P movement, insubstantial M/L movement, and substantial rotation.

BACKGROUND OF THE INVENTION

Total knee prostheses or knees can be divided into two general categories: fixed bearing, where the tibial insert is firmly attached to the baseplate with movement only between the femoral and tibial condylar surface; and mobile bearing, where the insert moves in relation to the baseplate as well as the femoral component. Mobile bearing knees can be further divided into two groups: a rotating platform type, in which the movement between the insert and baseplate is purely internal/external rotation; and the meniscal bearing type, which incorporates gliding in the A/P and M/L directions in addition to rotation.

After total knee replacement, failure is usually caused by loose or worn components. Loose components are caused by excessive loads being transferred to the implant/bone interface that causes interface bonding failure and the implants to loosen. With knee implants, these failures are commonly seen on the tibial side because the implant is susceptible to high shear loading. In a normal intact knee, these shear loads are resisted by soft tissue support and joint congruency.

In order to minimize the transfer of shear stresses to the implant/bone interface with a fixed bearing total knee replacement, the femoral component is allowed to freely slide on the tibia component, using soft tissue to provide constraint. In order to freely slide, these designs require low congruency between the femur and tibia resulting in low contact area. The low contact area causes high contact stresses and contact stresses shorten component life due to material fatigue.

The congruency between the femoral and tibial articulating surfaces of fixed bearing knees must be carefully balanced in order to provide maximum contact area, which lowers the stresses in the polyethylene, yet not be so constrained that normal movement of the femur on the tibia is hampered resulting in high shear stresses.

Mobile bearing knees were developed in an effort to replicate the normal biomechanics of the knee, maximizing the congruency between the tibio-femoral articulation and minimizing shear loading on the tibia. This is accomplished by allowing the tibial insert to be mobile with respect to the baseplate and configured to provide maximum contact area with the femur. These designs are indicated for patients who have adequate collateral ligamentous stability.

The Oxford Knee (Biomet) was an uni-compartmental knee that was the first to use the mobile bearing concept. The plastic "menisci" were totally unconstrained and were prone to dislocation. The LCS Knee (DePuy) was introduced shortly after the Oxford Knee and is the most widely used mobile bearing knee in the world and, having just marked its 20$^{th}$ year in clinical use, has the longest clinical experience with large numbers. The first LCS design as of the meniscal bearing type with two poly bearings that allowed retention of the ACL and/or PCL. These bearings allowed internal/external rotation and some A/P movement. This design has been fairly successful, although bearing dislocation and fractures have been problems. The second version of the LCS was the rotating only type that sacrificed both cruciate ligaments. This design has also enjoyed a good clinical track record, and because of fewer complications, is used more that the meniscal version of the LCS. A more recent version of the LCS has added A/P gliding.

Other mobile bearing knees in clinical use are: the Rotaglide Knee (Corin), which incorporates a single tibial insert that allows rotation and A/P movement and is approaching ten years of good clinical experience; and the TACK Knee (Link) which is a rotating platform. The more recent SAL (Sulzer) and MBK (Zimmer) Knees are single piece poly designs that allow A/P movement and rotation about a post centered mediolaterally on the baseplate. These two knees have good results at eight and five years, respectively. The Interax ISA (Howmedica) offers A/P movement with asymmetric rotation about a medialized post.

All of the newer designs have added A/P movement in an effort to improve on the rotating platform design or embrace the concept that mobile bearing total knee replacement should replicate, as much as possible, the natural biomechanics and kinematics of the knee while secondarily increasing the contact area of articulating surfaces.

BRIEF SUMMARY OF THE INVENTION

In accordance with the present invention, a mobile bearing knee prosthesis is provided having a femoral component having a femoral condylar surface, a tibial component, and a meniscal insert. The tibial component has an upper baseplate which includes an upstanding post, and a cap provided at an upper end of the post. The cap includes an extending lip extending laterally outward from the post whereby the cap has a generally oval shape in plan view with a major axis in the A/P direction and a minor axis in the M/L direction. The meniscal insert is disposed between the femoral condylar surface and the baseplate. The insert includes an undercut cavity which is elongated in the A/P direction and in which the post is received. The undercut cavity has a length in the A/P direction allowing substantial movement of the post therealong, and a width in the M/L direction allowing only a minor movement of the post in the M/L direction. The insert also includes an upper cutout extending around an upper portion of the cavity which is sized to receive therein an adjacent portion of the lip of the cap. With this construction, the insert and the baseplate are free to slide relative to one another along a plane of contact therebetween, except when constrained by (i) a contact of an adjacent portion of the post with a wall of the undercut cavity as movement occurs in the A/P and M/L directions of the plane of contact, whereby substantial relative movement of the insert and baseplate in the A/P direction is allowed and only a minor relative movement in the M/L direction is allowed, and (ii) an engagement of portions of the lip of the cap located between the minor axis and the major axis with a wall of the upper cutout as rotation occurs about an axis perpendicular to the plane of contact, whereby only some predetermined rotational relative movement is allowed.

In a preferred embodiment of the invention, the upper cutout includes straight portions provided between anterior and posterior ends thereof. The lip is then provided laterally with opposed pairs of flats. Respective flats of a pair are located in opposite quadrants and adjacent the minor axis. Thus, when the insert and baseplate are constrained by engagement of portions of the lip and the wall of the upper cutout, one pair of opposed flats engages adjacent straight portions of the upper cutout to provide a strong surface contact therebetween.

In the preferred embodiment, the cavity includes an anterior end and a posterior end. These ends are shaped congruently with respective anterior and posterior portions of the post. Thus, when extremes of anterior or posterior relative movement of the baseplate and the insert are experienced, about one half of the lip is received in the adjacent part of the upper cutout providing a large locking engagement to prevent separation of the insert from the baseplate.

Also in the preferred embodiment, the width of the cavity is slightly smaller than a minor diameter the lip such that the post is received in the cavity by a snap-fit of the lip past the width of the cavity. In addition, a lower edge of the undercut cavity is chamfered to provide an easy entrance of the lip of the cap upwards to the upper cutout.

Further in the preferred embodiment, the post is round in plan cross section. In addition, a difference between the minor diameter of the cap and a width of the cavity is less than 2 mm. Further, a height of the post is less than a depth of the cavity so that a space in the cavity is provided between the top of the cap and the overlying portion of the insert. Still further, the oval cap and the upper cutout of the cavity are configured to allow up to 30° of relative rotation of the baseplate and the insert.

It is an advantage of the present invention that rotation and A/P translation of the tibial component and insert of the knee prosthesis is allowed, while only a small M/L translation is simultaneously allowed, all with a simple post and cavity engagement.

It is also an advantage of the present invention that free movement of the tibial component and insert of a knee prosthesis is allowed in a normal range in three degrees of freedom, but this movement is limited at the extreme positions of movement desired, all with a simple post and cavity engagement.

It is another advantage of the present invention that separation of the tibial component and insert of the knee prosthesis at the extreme positions and otherwise is prevented by a mutual and strong interlocking of the tibial component and the insert.

It is still another advantage of the present invention that in the normal range of movement, engagement between a post of the tibial insert and the cavity walls of a cavity in the insert is avoided.

It is yet another advantage of the present invention that an easy and secure snap fit of the post of the tibial component in the cavity of the meniscal insert is provided.

Other features and advantages of the present invention are stated in or apparent from detailed descriptions of presently preferred embodiments of the invention found hereinbelow.

BRIEF DESCRIPTION OF THE SEVERAL VIEWS OF THE DRAWING

FIG. 1 is a front elevation view of a knee prosthesis of the present invention in a neutral position.

FIG. 2 is a left side view of the knee prosthesis depicted in FIG. 1.

FIG. 3 is a left side cross section view of the knee prosthesis depicted in FIG. 1 taken along the line 3—3.

FIG. 4 is a plan cross section view of the knee prosthesis depicted in FIG. 1 taken along the line 4—4.

FIG. 5 is a front cross section view of the knee prosthesis depicted in FIG. 1 taken along the line 5—5 in FIG. 2.

FIG. 6 is a rear elevation view of the tibial component depicted in FIG. 1.

FIG. 7 is a (rotated) top plan view of the tibial component depicted in FIG. 6.

FIG. 7A is a blown up top plan view of the cap depicted in FIG. 7.

FIG. 8 is a bottom plan view of the meniscal insert depicted in FIG. 1.

FIG. 9 is a front elevation view of the meniscal insert depicted in FIG. 8.

FIG. 10 is a top plan view of the meniscal insert depicted in FIG. 8.

FIG. 11 is a front cross section view of the meniscal insert depicted in FIG. 8 taken along the section line 11—11.

FIG. 12 is a left side cross section view of the meniscal insert depicted in FIG. 9 taken along the section line 12—12.

FIG. 13 is a front elevation view of a knee prosthesis of the present invention in an extreme rotational movement position.

FIG. 14 is a left side view of the knee prosthesis depicted in FIG. 13.

FIG. 15 is a left side cross section view of the knee prosthesis depicted in FIG. 13 taken along the section line 15—15.

FIG. 16 is a plan cross section view of the knee prosthesis depicted in FIG. 13 taken along the section line 16—16.

FIG. 17 is a front elevation view of a knee prosthesis of the present invention in an extreme A/P movement position.

FIG. 18 is a left side view of the knee prosthesis depicted in FIG. 17.

FIG. 19 is a left side cross section view of the knee prosthesis depicted in FIG. 17 taken along the section line 19—19.

FIG. 20 is an enlarged view of the portion of FIG. 19 identified with dotted circle 20.

FIG. 21 is a plan cross section view of the knee prosthesis depicted in FIG. 17 taken along the section line 21—21.

DETAILED DESCRIPTION OF THE INVENTION

With reference now to the drawings in which like numerals represent like elements throughout the views, a mobile bearing knee prosthesis 20 of a single poly component meniscal bearing type is depicted in FIG. 1. Knee prosthesis 20 includes a tibial component 22, a meniscal insert 24 and a femoral component 26 having a femoral condylar surface 28. Femoral component 26 is depicted with a dash-dot line in FIG. 1 and may be shaped and made from a metal or ceramic in accordance with various configurations well known in the art. Femoral component 26 is omitted from the remainder of the figures for convenience and so as not to obstruct the depictions of the remaining elements. Also for convenience, the conventional three degrees of freedom of movement provided by knee prosthesis 20 will be referred to as follows: the anterior/posterior direction of knee prosthesis 10 will be referred to as the A/P direction, the medial/lateral direction as the M/L direction, and the rotation about a conventional vertical (up/down) axis as the rotational direction.

As shown in better detail in FIGS. 6–7, tibial component 22 includes a lower fixing stem 30 (which is an optional element as known in the art and thus may be omitted as desired) and a baseplate 32. Fixing stem 30 and baseplate 32, as well as the remainder of tibial component 22 are integrally made from a metal or ceramic as also well known in the art. Upstanding vertically from baseplate 32 is a post 34.

As shown best in FIG. 7, post 34 has a round shape in plan view. Provided at an upper end or top 40 of post 34 is a cap 41. Cap 41 includes a lip 42 extending laterally outward from post 34 to a lateral side. Lip 42 is configured so that cap 41 has a generally oval or elliptical shape in plan view, with a major axis 36 extending the A/P direction and a minor axis 3 8 extending in the M/L direction. As shown best in FIG. 7, the lateral side of cap 41 includes paired flats 44a, 44b and 46a, 46b which are located in opposite quadrants defined by axes 36 and 3 8 so as to be opposite to one another. The transitions between flats 44 and 46 with the remainder of the lateral side of lip 42 are smooth arcs, so that no sharp edges are located along the lateral side of lip 42.

Meniscal insert 24 is made of a suitable plastic and is located between femoral condylar surface 28 of femoral component 16 and baseplate 32 of tibial component 22, as known in the art. Insert 24 is designed to allow a free but limited relative movement (in the three degrees of freedom) with respect to baseplate 32 along the plane of contact with baseplate 32 as also well known in the art. The neutral position of prosthesis 20 about which limited relative movements of baseplate 32 and insert 24 are permitted in the three degrees of freedom is shown in FIGS. 1–5; while an extreme rotational movement is shown in FIGS. 13–16 and an extreme A/P movement is shown in FIGS. 17–21.

As shown in better detail in FIGS. 8–12, meniscal insert 24 includes an undercut cavity 50 provided in the bottom surface thereof facing baseplate 32. Cavity 50 is elongated in the A/P direction and is sized widthwise to receive lip 42 of post 34 with a snap-fit therein as discussed subsequently. As best shown in FIGS. 3–5, cavity 50 is also sized with a length to allow a substantial normal movement of post 34 in the A/P direction (e.g., about +5 mm to –2 mm), and with a width to allow only minor normal movement of post 34 in the M/L direction (e.g., about 1–2 mm total). The exact amount of A/P movement can be best determined as known in the art from the literature, cadaver kinematic testing and geometric constraints.

As shown best in the cross sectional views, such as in FIGS. 11–12, extending around an upper portion of cavity 50 is an upper cutout 52. Upper cutout 52 is sized and positioned to receive therein any adjacent portion of lip 42 of post 34, and with the width of cavity 50 being less than the minor axis diameter of lip 42, some M/L portion of lip 42 on both M/L sides thereof is always located in cutout 52 as shown in the various figures. A height of post 34 is less than a depth of cavity 50 so that a space 54 in cavity 50 is provided between the top 40 of post 34 and the overlying portion of insert 24. A chamfer 55 is also provided along a lower portion of cavity 50. Chamfer 55 provides a centering action when it is desired to position post 34 in cavity 50 with a snap-fit of lip 42 past chamfer 55 into upper cutout 52. Due to this centering action, the snap-fit is easily accomplished by simple finger pressure. However, as there is no centering action of lip 42 in upper cutout 52, lip 42 is securely held in upper cutout 52 and is not easily snapped or pulled out of upper cutout 52.

Undercut cavity 50 includes an anterior end 56 and a posterior end 58. Both ends 56 and 58 are shaped congruently with the adjacent (and matching) anterior and posterior portions of post 34. Thus, when extremes of anterior or posterior relative movement of baseplate 32 and insert 24 are unavoidably experienced as shown in FIGS. 17–21, there is a substantial and tight surface contact between post 34 and the wall of cavity 50 to oppose further movement. In addition, at the extreme positions, about one half of lip 42 is received in the adjacent part of upper cutout 52. This provides a large locking engagement to prevent a rocking separation of insert 24 from baseplate 32. Provided between ends 56 and 58 are straight portions 60 along which post 34 thus readily slides as required.

It will also be appreciated that due to the oval shape of cap 41 and the limited width of upper cutout 52 of cavity 50, rotation of post 34 in cavity 50 is also restricted to a predetermined range as desired, such as a normal range of less than ±30° and preferably about ±25°. As shown in FIGS. 1–5, the normal positional alignment of minor axis 38 is with the longitudinal axis of upper cutout 52 of cavity 50. At the limits of the normal rotation, as depicted in FIGS. 13–16, post 34 is turned to one side (or the other) so that the lateral clearance between lip 42 of cap 41 and upper cutout 52 of cavity 50 is eliminated. At this extreme rotation, one pair of flats 44a, 44b or 46a, 44b of lip 52 (depending on the direction of rotation) comes to bear against the adjacent straight portions 62 of upper cutout 52 of cavity 50 so that a surface bearing contact is effected to securely prevent further rotation and to spread the forces of contact over a larger area to prevent damage to either lip 42 or upper cutout 52.

It will thus be appreciated that during normal movements in the A/P and rotational directions, free movement with little friction and debris wear is obtained as little contact is made between the wall of cavity 50 and the adjacent portion of post 34 or between upper cutout 52 and the adjacent portion of lip 42; while movement in the M/L direction is largely prevented with little friction or wear as the wall of cavity 50 contacts the adjacent portion of post 34.

Post 34 of tibial component 22 has been depicted and described as being round. However, it would be possible to provide post 34 with an oval or other shape so long as this shape did not interfere with the positioning of flats 44 or 46 against straight portions 62 in preventing rotation beyond that desired. Similarly, cap 42 has been depicted and described as having a generally oval or elliptical shape. However, it would be possible to provide cap 42 with more of an egg shape other shape so long as the shape provided the necessary sides to prevent rotation beyond the desired amount.

While the present invention has been described with respect to an exemplary embodiments thereof, it will be understood by those of ordinary skill in the art that variations and modifications can be effected within the scope and spirit of the invention.

I claim:

1. A mobile bearing knee prosthesis comprising:
   a femoral component having a femoral condylar surface;
   a tibial component having an upper baseplate, said baseplate including
   (a) an upstanding post, and
   (b) a cap provided at an upper end of said post, said cap including an extending lip extending laterally outward from said post whereby said cap has a generally oval shape in plan view with a major axis in the A/P direction and a minor axis in the M/L direction; and
   a meniscal insert disposed between said femoral condylar surface and said baseplate, said insert including
   (a) an undercut cavity which is elongated in the A/P direction and in which said post is received, said undercut cavity having a length in the A/P direction allowing substantial movement of said post therealong and a width in the M/L direction allowing only a minor movement of said post in the M/L direction, and (b) an upper cutout extending around an upper portion of said cavity which is sized to receive therein an adjacent portion of said lip of said cap;

wherein said insert and said baseplate are free to slide relative to one another along a plane of contact therebetween, except when constrained by (i) a contact of an adjacent portion of said post with a wall of said undercut cavity as movement occurs in the A/P and M/L directions of the plane of contact, whereby substantial relative movement of said insert and baseplate in the A/P direction is allowed and only a minor relative movement in the M/L direction is allowed, and (ii) an engagement of portions of said lip of said cap located between said minor axis and said major axis with a wall of said upper cutout as rotation occurs about an axis perpendicular to the plane of contact, whereby only some predetermined rotational relative movement is allowed.

2. A mobile bearing knee prosthesis as claimed in claim 1:

wherein said upper cutout includes straight portions provided between anterior and posterior ends thereof; and wherein said lip is provided laterally with opposed pairs of flats, respective flats of a said pair being located in opposite quadrants and adjacent the minor axis such that when said insert and baseplate are constrained by engagement of portions of said lip and the wall of said upper cutout, one pair of opposed flats engages adjacent straight portions of said upper cutout to provide a strong surface contact therebetween.

3. A mobile bearing knee prosthesis as claimed in claim 2:

wherein said cavity includes an anterior end and a posterior end, with said anterior and posterior ends shaped congruently with respective anterior and posterior portions of said post, whereby when extremes of anterior or posterior relative movement of said baseplate and said insert are experienced, about one half of said lip is received in the adjacent part of said upper cutout providing a large locking engagement to prevent separation of said insert from said baseplate.

4. A mobile bearing knee prosthesis as claimed in claim 1:

wherein the width of said cavity is slightly smaller than a minor diameter said lip such that said post is received in said cavity by a snap-fit of said lip past the width of said cavity.

5. A mobile bearing knee prosthesis as claimed in claim 4:

wherein a lower edge of said undercut cavity is chamfered to provide an easy entrance of said lip of said cap upwards to said upper cutout.

6. A mobile bearing knee prosthesis as claimed in claim 1:

wherein said post is round in plan cross section.

7. A mobile bearing knee prosthesis as claimed in claim 1:

wherein a difference between the minor diameter of said cap and a width of said cavity is less than 2 mm.

8. A mobile bearing knee prosthesis as claimed in claim 1:

wherein a height of said post is less than a depth of said cavity so that a space in said cavity is provided between the top of said cap and the overlying portion of said insert.

9. A mobile bearing knee prosthesis as claimed in claim 1:

wherein said cavity includes an anterior end and a posterior end, with said anterior and posterior ends shaped congruently with respective anterior and posterior portions of said post, whereby when extremes of anterior or posterior relative movement of said baseplate and said insert are experienced, about one half of said lip is received in the adjacent part of said upper cutout providing a large locking engagement to prevent separation of said insert from said baseplate.

10. A mobile bearing knee prosthesis as claimed in claim 1:

wherein said oval cap and said upper cutout of said cavity are configured to allow up to 30° of relative rotation of said baseplate and said insert.

* * * * *